US008912149B1

(12) United States Patent
Rawat et al.

(10) Patent No.: US 8,912,149 B1
(45) Date of Patent: Dec. 16, 2014

(54) GLYCOSAMINOGLYCAN MIMETICS

(75) Inventors: Manish Rawat, Hinjewadi (IN); Linda Hsieh-Wilson, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 1185 days.

(21) Appl. No.: 12/315,168

(22) Filed: Nov. 28, 2008

Related U.S. Application Data

(60) Provisional application No. 61/004,581, filed on Nov. 28, 2007.

(51) Int. Cl.
*A01N 43/04* (2006.01)
*A61K 31/70* (2006.01)
*C08B 37/00* (2006.01)
*A61K 47/48* (2006.01)
*C08G 61/12* (2006.01)

(52) U.S. Cl.
CPC .......... *A61K 47/48092* (2013.01); *C08G 61/12* (2013.01)
USPC .......................................... 514/23; 526/238.2

(58) Field of Classification Search
CPC .................. A61K 47/48092; A61K 47/48176; A61K 47/48023; C08G 61/12
USPC .......................................... 514/23; 526/238.2
See application file for complete search history.

(56) References Cited

U.S. PATENT DOCUMENTS

| | | | |
|---|---|---|---|
| 4,376,110 A | 3/1983 | David et al. | |
| 4,399,216 A | 8/1983 | Axel et al. | |
| 4,740,461 A | 4/1988 | Kaufman | |
| 4,883,751 A | 11/1989 | Gitel et al. | |
| 4,912,040 A | 3/1990 | Kaufman et al. | |
| 4,946,778 A | 8/1990 | Ladner et al. | |
| 4,959,455 A | 9/1990 | Clark et al. | |
| 5,185,245 A | 2/1993 | Heimer | |
| 5,587,442 A * | 12/1996 | Kiessling et al. | 526/238.2 |
| 5,821,337 A | 10/1998 | Carter et al. | |
| 6,200,564 B1 | 3/2001 | Lamont et al. | |
| 6,291,616 B1 * | 9/2001 | Kiessling et al. | 526/171 |
| 6,680,304 B2 | 1/2004 | Pahi et al. | |
| 7,638,503 B2 | 12/2009 | Hsieh-Wilson et al. | |
| 2003/0073147 A1 | 4/2003 | Alderete et al. | |
| 2005/0180945 A1* | 8/2005 | Chaikof et al. | 424/78.27 |
| 2006/0025379 A1 | 2/2006 | Hsieh-Wilson et al. | |
| 2007/0275412 A1 | 11/2007 | Gama et al. | |
| 2008/0009607 A1 | 1/2008 | Tully et al. | |
| 2008/0124339 A1 | 5/2008 | Pullen et al. | |
| 2010/0071080 A1 | 3/2010 | Tully et al. | |
| 2010/0075920 A1 | 3/2010 | Hsieh-Wilson et al. | |

FOREIGN PATENT DOCUMENTS

| | | | |
|---|---|---|---|
| WO | WO 92/22653 A1 | 12/1992 | |
| WO | WO 93/21319 A1 | 10/1993 | |
| WO | WO 03/002125 A2 | 9/2003 | |
| WO | WO 03/002125 A3 | 11/2003 | |
| WO | WO 2004/017910 A2 | 3/2004 | |
| WO | WO 2004/017910 A3 | 9/2004 | |

OTHER PUBLICATIONS

Vippagunta, S.R., Brittain, H.G., Grant, D.J.W. (2001) Crystalline solids. Advanced Drug Delivery Reviews, vol. 48, pp. 3-26.*
Morissette, S.L., Almarsson, Ö., Peterson, M.L., Remenar, J.F., Read, M.J., Lemmo, A.V., Ellis, S., Cima, M.J., Gardner, C.R. (2004) High-throughput crystallization: polymorphs, salts, co-crystals and solvates of pharmaceutical solids. Advanced Drug Delivery Reviews, vol. 56, pp. 275-300.*
Maeda, N., Fukazawa, N., Hata, T. (2006) The Binding of Chondroitin Sulfate to Pleiotrophin/Heparin-Binding Growth-Associated Molecule is Regulated by Chain Length and Oversulfated Structures. The Journal of Biological Chemistry, vol. 281, No. 8, p. 4894-4902.*
Lu, K.V., Jong, K.A., Kim, G.Y., Singh, J., Dia, E.Q., Yoshimoto, K., Wang, M.Y., Cloughesy, T.F., Nelson, S.F., Mischel, P.S. (2005) Differential Induction of Glioblastoma Migration and Growth by Two Forms of Pleiotrophin. The Journal of Biological Chemistry, vol. 280, No. 29, p. 26953-26964.*
Office action date Jun. 2, 2011 for JP Application No. 2007-515442 (in Japanese with English translation).
Belot, et al. Unexpected stereochemical outcome of activated 4,6-O-benzylidene derivatives of the 2-deoxy-2-trichloroacetamido-D-galacto series in glycosylation reactions during the synthesis of a chondroitin 6-sulfate trisaccharide methyl glycoside. Carb. Res. (2000) 325:93-106.
Bergefell, et al. Chondroitin sulfate characterized by the E-disaccharide unit is a potent inhibitor of herpes simplex virus infectivity and provides the virus binding sites on gro2C cells. J Biol Chem. Sep. 16, 2005; 280(37):32193-9.
Blatter, et al. The use of 2-deoxy-2-trichloroacetamido-D-glucopyranose derivatives in synthesis of oligosaccharides. Carb. Res. (1994) 260:189-202.
Bradbury, et al. Chondroitinase ABC promotes function recovery after spinal cord injury. Nature. 2002; 416:636-640.
Brittis, et al. Chondroitin sulfate as a regulator of neuronal patterning in the retina. Science. 1992; 255:733-736.
Caldas, et al. Humanization of the anti-CD18 antibody 6.7: an unexpected effect of a framework residue in binding to antigen. Mol Immunol. May 2003; 39(15):941-52.
Campbell (Monoclonal Antibody Technology, Laboratory Techniques in Biochemistry and Molecular Biology, Elsevier Science Publishers B.V.: Amsterdam, The Netherlands, vol. 13, pp. 1-32, 1984).
Chien, et al. Significant structural and functional change of an antigen-binding site by a distant amino acid substitution: proposal of a structural mechanism. Proc Natl Acad Sci U S A. Jul. 1989; 86(14):5532-6.

(Continued)

*Primary Examiner* — Scarlett Goon
(74) *Attorney, Agent, or Firm* — Wilson Sonsini Goodrich & Rosati

(57) ABSTRACT

The present invention provides composition comprising one or more glycosaminoglycan mimetics and uses thereof. The subject glycosaminoglycan mimetics are particularly useful for treatment of neuronal injuries including without limitation spinal cord injuries.

32 Claims, 6 Drawing Sheets

(56) References Cited

OTHER PUBLICATIONS

Cote, et al. Generation of human monoclonal antibodies reactive with cellular antigens. Proc Natl Acad Sci U S A. Apr. 1983;80(7):2026-30.

Cote, et al. The EBV-Hybridoma technique and its application to human lung cancer. In Monoclonal antibodies and cancer therapy. Alan R. Liss, Inc. 1985; 77-96.

Dou, et al. Differential effects of glycosaminoglycans on neurite growth on laminin and L1 substrates. J. Neurosci. 1995; 15:8053-8066.

Emerling, et al. nhibitors and promoters of thalamic neuron adhesion and outgrowth in embryonic neocortex: functional association with chondroitin sulfate. Neuron. 1996; 17:1089-1100.

Falshaw, et al. Comparison of the glycosaminoglycans isolated from the skin and head cartilage of Gould's arrow squid (*Nototodarus gouldi*). Carbohydrate Polymers. 2000; 41:357-364.

Fournier, et al. Identification of a receptor mediating Nogo-66 inhibition of axonal regeneration. Nature. Jan. 18, 2001; 409(6818):341-6.

Fundamental Immunology p. 242 (William E. Paul, M.D. ed., 3d ed; 1993.

Gama, et al. Sulfation patterns of glycosaminoglycans encode molecular recognition and activity. Nat Chem Biol. Sep. 2006; 2(9):467-73.

Garland, Ed. Immunobiology. Janeway, 2001, pp. 102-103.

Garrett and Grisham. "Biochemistry" Published 1999 by Saunders College Publishers, p. 236.

Giusti, et al. Somatic diversification of S107 from an antiphosphocholine to an anti-DNA autoantibody is due to a single base change in its heavy chain variable region. Proc Natl Acad Sci U S A. May 1987; 84(9):2926-30.

Green, et al. Antigen-specific human monoclonal antibodies from mice engineered with human Ig heavy and light chain YACs. Nat Genet. May 1994; 7(1):13-21.

Greene, et al. Protective Groups in Organic Synthesis. Published by John Wiley and Sons. 1999; pp. 67-74.

Gussow, et al. Humanization of monoclonal antibodies. Methods Enzymol. 1991; 203:99-121.

Habeeb, A. F. Determination of free amino groups in proteins by trinitrobenzenesulfonic acid. Anal Biochem. Mar. 1966;14(3):328-36.

Habuchi, et al. Enzymatic synthesis of chondroitin sulfate E by N-acetylgalactosamine 4-sulfate 6-O-sulfotransferase purified from squid cartilage. An Bio. 2002; 310(2):129-136.

Holm, et al. Functional mapping and single chain construction of the anti-cytokeratin 8 monoclonal antibody TS1. Mol Immunol. Feb. 2007;44(6):1075-84.

Holt, et al. Sugar codes for axons? Neuron. Apr. 21, 2005;46(2):169-72.

Huse, et al. Generation of a large combinatorial library of the immunoglobulin repertoire in phage lambda. Science. Dec. 8, 1989;246(4935):1275-81.

Immunobiology for life scientists (Wiley, Ed. Eales, p. 14, 2003.

International preliminary report on patentability dated Nov. 29, 2006 for PCT Application No. US2005/018906.

International searh report dated Mar. 10, 2006 for PCT Application No. US2005/018906.

Ito, et al. Structural characterization of the epitopes of the monoclonal antibodies 473HD, CS-56, and MO-225 specific for chondroitin sulfate D-type using the oligosaccharide library. Glycobiology. Jun. 2005;15(6):593-603.

Iyer, et al. Design and synthesis of hyaluronan-mimetic Gemini disaccharides. Tetrahedron (2003) 59:631-638.

Jacquinet, et al. Multigram syntheses of the disaccharide repeating units of chondroitin 4- and 6-sulfates. Carbohydr-Res. Dec. 31, 1998; 314(3-4): 283-8.

Jacquinet, J. Synthesis of the methyl glycosides of the repeating units of chondroitin 4- and 6-sulfate. Carb. Res. (1990) 199:153-181.

Kalovidouris, et al. A role for fucose a (1-2) galactose carbohydrates in neuronal growth. J. Am. Chem. Soc. 2005; 127:1340-1341.

Karst, et al. Chemical synthesis of β-D-GlcpA(2SO4)-(1->3)-D-GalpNAc(6SO4), the disaccharide repeating unit of shark cartilage chondroitin sulfate D, and of its methyl β-D-glycoside derivative. J. Chem. Soc. Perkin Trans. 2000; 1:2709-2717.

Karst, et al. Stereocontrolled total syntheses of shark cartilage chondroitin sulfate D-related tetra- and hexasaccharide methyl glycosides. Eur. J. Org. Chem. 2002; 815-825.

Kitagawa, et al. Developmental regulation of the sulfation profile of chondroitin sulfate chains in the chicken embryo brain. J Biol Chem. Dec. 12, 1997;272(50):31377-81.

Kohler, et al. Continuous cultures of fused cells secreting antibody of predefined specificity. Nature. Aug. 7, 1975;256(5517):495-7.

Koshiishi, et al. Analysis of chondroitin sulfate/dermatan sulfate chains in rat peritoneal resident macrophages. J. Biol. Pharm. Bull. 1993; 16:307-308.

Kozbor, et al. The production of monoclonal antibodies from human lymphocytes. Immunology Today. 1983; 4:72-79.

Lucas, et al. Synthesis of heparin-like pentamers containing "opened" uronic acid moieties. Tetrahedron. 1990; 46:8207-8228.

MacCallum, et al. Antibody-antigen interactions: contact analysis and binding site topography. J Mol Biol. Oct. 11, 1996;262(5):732-45.

Maggio (Immunoenzyme technique I, CRC press 1980, pp. 186-187).

Mariuzza, et al. The structural basis of antigen-antibody recognition. Annu Rev Biophys Biophys Chem. 1987;16:139-59.

Marra, et al. Synthesis of disaccharide fragments of dermatan sulfate. Carb. Res. 1989; 195:39-50.

Marsh, et al. Signal transduction events mediated by the BDNF receptor gp 145trkB in primary hippocampal pyramidal cell culture. J Neurosci. Oct. 1993;13(10):4281-92.

Mizuguchi, et al. Chondroitin proteoglycans are involved in cell division of *Caenohabditis elegans*. Nature. 2003; 423:443-448.

Moon, et al. Regeneration of CNS axons back to their target following treatment of adult rat brain with chondroitinase ABC. Nat Neurosci. May 2001;4(5):465-6.

Nadanaka, et al. Characteristic hexasaccharide sequences in octasaccharides derived from shark cartilage chondroitin sulfate D with a neurite outgrowth promoting activity. J. Biol. Chem. 1998; 273:3296-3307.

Nandini, et al. Structural and functional characterization of oversulfated chondroitin sulfate/dermatan sulfate hybrid chains from the notochord of hagfish. Neuritogenic and binding activities for growth factors and neurotrophic factors. J Biol Chem. Dec. 3, 2004;279(49):50799-809.

Plaas, et al. Glycosaminoglycan sulfation in human osteoarthritis. Disease-related alterations at the non-reducing termini of chondroitin and dermatan sulfate. J Biol Chem. May 15, 1998;273(20):12642-9.

Rudikoff, et al. Single amino acid substitution altering antigen-binding specificity. Proc Natl Acad Sci U S A. Mar. 1982;79(6):1979-83.

Sandson, et al. The potential application of cyclo-oxygenase type 2 inhibitors to Alzheimer's disease. Expert Opin Investig Drugs. Apr. 1998;7(4):519-26.

Shi, et al. Luteolin sensitizes tumor necrosis factor-alpha-induced apoptosis in human tumor cells. Oncogene. Oct. 7, 2004;23(46):7712-21.

Shipp, et al. Profiling the sulfation specificities of glycosaminoglycan interactions with growth factors and chemotactic proteins using microarrays. Chem Biol. Feb. 2007;14(2):195-208.

Shirayev, et al. Synthesis of Novel Adamantylalkoxyurea Derivatives from 2-(1-Adamantylimino)-1,3-oxathiolane. Journal of Synthetic Organic Chemistry. 1997; 1:38-40.

Smetsers, et al. Human Single-Chain Antibodies Reactive with Native Chondroitin Sulfate Detect Chondroitin Sulfate Alterations in Melanoma and Psoriasis. J Invest Dermatol. Mar. 2004;122(3):707-16.

Sotogaku, et al. Activation of phospholipase C pathways by a synthetic chondroitin sulfate-E tetrasaccharide promotes neurite outgrowth of dopaminergic neurons. J Neurochem. Oct. 2007;103(2):749-60.

(56) References Cited

OTHER PUBLICATIONS

Stevens, et al. Synthesis of chondroitin sulfate E glycosaminoglycan onto p-nitrophenyl-β-d-xyloside and its localization to the secretory granules of rat serosal mast cells and mouse bone marrow-derived mast cells. JBC.1983; 258;5977-5984.

Sugahara, et al. Recent advances in the structural biology of chondroitin sulfate and dermatan sulfate. Curr. Opin. Chem. Biol. 2003; 13:612-620.

Sugahara, et al. Structural studies on the chondroitinase ABC-resistant sulfated tetrasaccharides isolated from various chondroitin sulfate isomers. Carbohydr Res. Mar. 4, 1994;255:145-63.

Suzuki, et al. Formation of three types of disulfated disaccharides from chondroitin sulfates by chondroitinase digestion. J Biol Chem. Apr. 10, 1968;243(7):1543-50.

Takagaki, et al. Domain structure of chondroitin sulfate E octasaccharides binding to type V collagen. J Biol Chem. Mar. 15, 2002;277(11):8882-9.

Tamura, et al. A regio- and stereoselective synthesis of 4-0-sulfated chondroitin di-and tetrasaccharides based on the strategy designed for the elongation of the repeating unit. Bioorg. Medic. Chem. Lett. 1995; 5:1351-1354.

Tamura, et al. Synthetic approach towards sulfated chondroitin di-, tri- and tetrasaccharides corresponding to the repeating unit. Carb. Res. 1998; 305:43-63.

Taylor, et al. A colorimetric method for the quantitation of uronic acids and a specific assay for galacturonic acid. Anal Biochem. Feb. 14, 1992;201(1):190-6.

Tsuchida, et al. Appican, the proteoglycan form of the amyloid precursor protein, contains chondroitin sulfate E in the repeating disaccharide region and 4-O-sulfated galactose in the linkage region. J. Biol. Chem. 2001; 276:37155-37160.

Tully, et al. A chondroitin sulfate small molecule that stimulates neuronal growth. J. Am. Chem. Soc. 2004; 126:7736-7737.

Tully, et al. Discovery of a TNF-alpha antagonist using chondroitin sulfate microarrays. J Am Chem Soc. Jun. 21, 2006;128(24):7740-1.

Volpi, N. Disaccharide mapping of chondroitin sulfate of different origins by high-performance capillary electrophoresis and high-performance liquid chromatography. Carbohyd. Polym. 2004; 55, 273-281.

Winkler, et al. Changing the antigen binding specificity by single point mutations of an anti-p24 (HIV-1) antibody. J Immunol. Oct. 15, 2000;165(8):4505-14.

Yamagata, et al. A monoclonal antibody that specifically recognizes a glucuronic acid 2-sulfate-containing determinant in intact chondroitin sulfate chain. J Biol Chem. Mar. 25, 1987;262(9):4146-52.

Yamagata, et al. Tissue variation of two large chondroitin sulfate proteoglycans (PG-M/versican and PG-H/aggrecan) in chick embryos. Anat Embryol (Berl). May 1993;187(5):433-44.

Yeung, et al. An essential role for the interferon-inducible, double-stranded RNA-activated protein kinase PKR in the tumor necrosis factor-induced apoptosis in U937 cells. Proc Natl Acad Sci U S A. Oct. 29, 1996;93(22):12451-5.

Zhang, et al. DDQ-mediated oxidation of 4,6-O-methoxybenzylidene-protected saccharides in the presence of various nucleophiles: formation of 4-OH, 6-Cl, and 6-Br derivatives. J. Org. Chem. 1996; 61:2394-2400.

Fukui, et al. Oligosaccharide microarrays for high-throughput detection and specificity assignments of carbohydrate-protein interactions. Nat Biotechnol. Oct. 2002;20(10):1011-7. Epub Sep. 3, 2002.

Kinoshita, et al. Isolation and structural determination of novel sulfated hexasaccharides from squid cartilage chondroitin sulfate E that exhibits neuroregulatory activities. Biochemistry. Oct. 23, 2001;40(42):12654-65.

\* cited by examiner

*a* Conditions: (a) TMSOTf, CH$_2$Cl$_2$, −20 °C, 69%. (b) HF·pyr, THF/pyr, 25 °C, 95%. (c) AIBN, Bu$_3$SnH, benzene, 50 °C, 92%. (d) DDQ, CH$_3$CN/H$_2$O, 25 °C, 89%. (e) SO$_3$·TMA, DMF, 80 °C, 85%. (f) (i) HF·pyr, THF/pyr, 25 °C; (ii) LiOH, H$_2$O$_2$, then NaOH, MeOH, 25 °C, 89% (two steps).

[a] Conditions: (a) 8, 1:5 MeOH/(CH$_2$Cl)$_2$, 55 °C, 24 h. (b) TMSOTf, 4, CH$_2$Cl$_2$, −20 °C, 45%. (c) AIBN, Bu$_3$SnH, benzene, 50 °C, 89%. (d) DDQ, CH$_3$CN/H$_2$O, 25 °C. (e) SO$_3$·TMA, DMF, 80 °C, 71% (two steps).

$^a$ Conditions: (a) (i) HF·pyr, THF/pyr, 25 °C; (ii) LiOH, H$_2$O$_2$, then NaOH, MeOH, 25 °C, 87–97% (two steps).

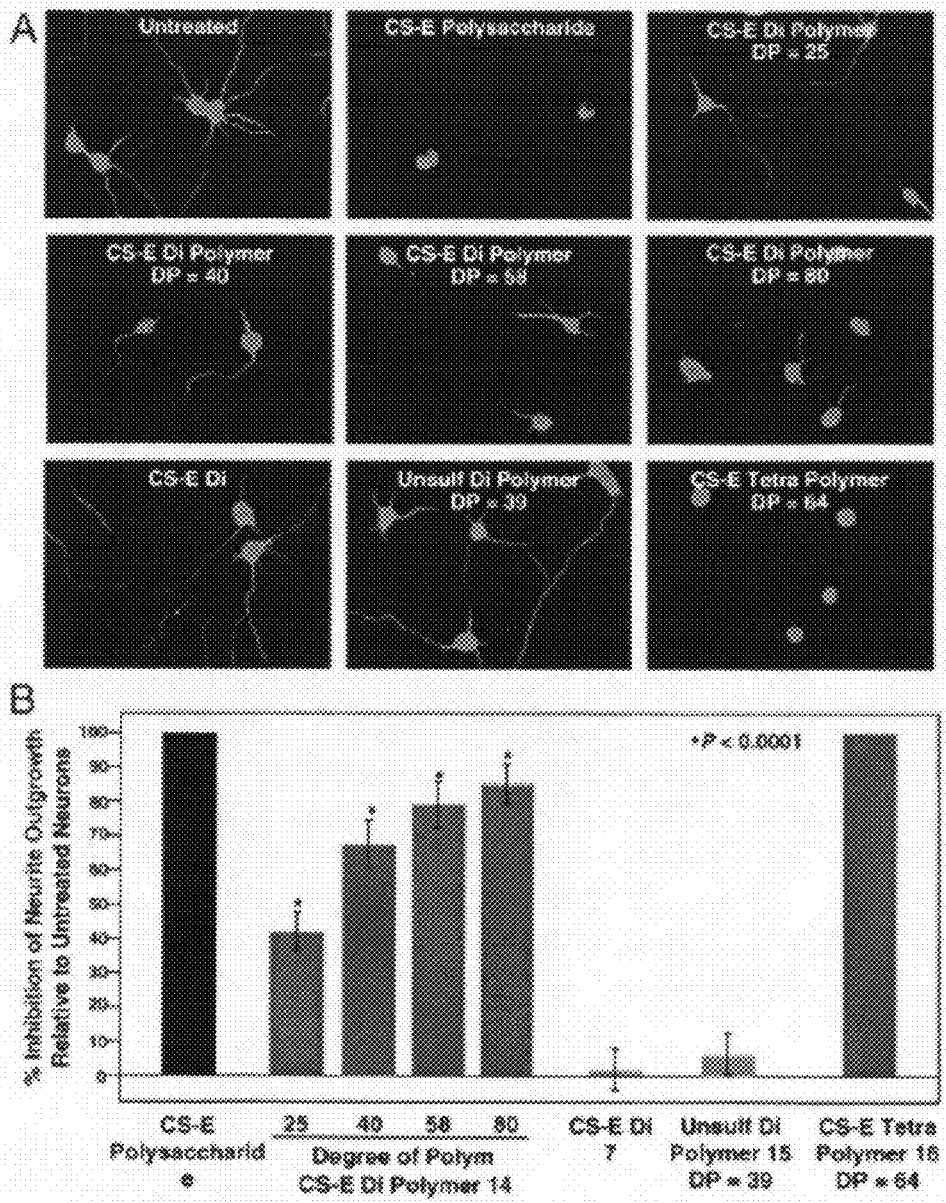

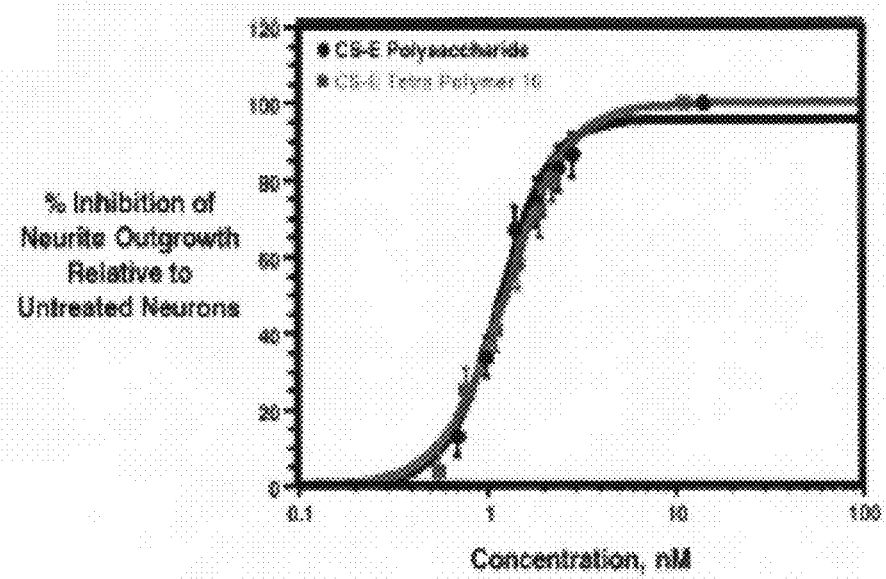

GLYCOSAMINOGLYCAN MIMETICS

CROSS-REFERENCE

This application claims the benefit of U.S. Provisional Application No. 61/004,581, filed Nov. 28, 2007, which application is incorporated herein by reference.

BACKGROUND OF THE INVENTION

Glycosaminoglycans such as chondroitin sulfate (CS) play a critical role in various physiological processes, including cell division, inflammation, and spinal cord injury. However, the complexity of this class of natural molecules has made correlating structure to function difficult. Furthermore, it has not been retrieval to generate glycosaminoglycan with controllable sulfation pattern.

Comprising 40-200 sulfated disaccharide units, CS is thought to contain "blocks" of high and low sulfation, with highly sulfated regions serving as binding sites for growth factors, cytokines, and other proteins. Although a tetrasaccharide can be sufficient for molecular recognition and neuronal activity, longer sequences are thought to be useful for enhancing protein binding and allowing for the assembly of multimeric protein complexes.

Thus far very few polymers based on glycosaminoglycan structures have been reported. Heparin-like glycopolymers have been synthesized from simple monosaccharides such as N-acetyl-D-glucosamine. However, no high molecular weight glycopolymers have been assembled from disaccharide building blocks found in heparin/heparan sulfate, chondroitin, dermatan, or keratan sulfate glycosaminoglycans. Such glycopolymers would more closely mimic the natural polysaccharides, and hence facilitating explorations into the importance of macromolecular structure (e.g., distance, number, and orientation between protein-binding epitopes, multivalency).

SUMMARY OF THE INVENTION

There remains an unmet need for the development of CS mimetics that would retain key properties of glycosaminoglycan polysaccharides. Accordingly, described herein are the synthesis and characterization of CS glycopolymers with controllable sulfation sequence and tunable chemical and biological properties.

In one embodiment, the present invention provides a multivalent sulfated glycosaminoglycan mimetic that inhibits or stimulates neural growth with an EC50 of about 10 uM, 5 uM, 1 uM, 50 nM, 25 nM, 5 nM or less when assayed in an in vitro assay. In another embodiment, the present invention provides a composition comprising a population of substantially homogeneous glycosaminoglycan mimetics, wherein individual members of said glycosaminoglycan mimetics are of a formula W, X, Y, or Z,
wherein W is:

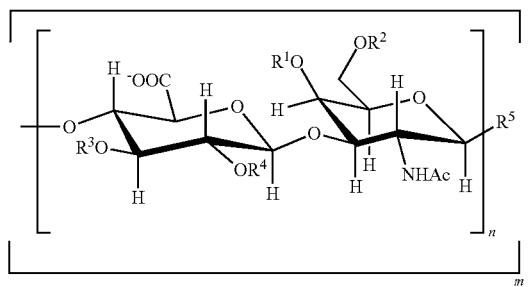

wherein X is:

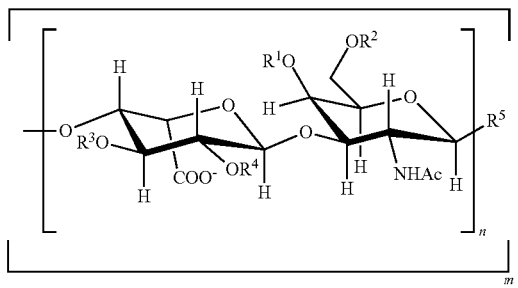

wherein Y is:

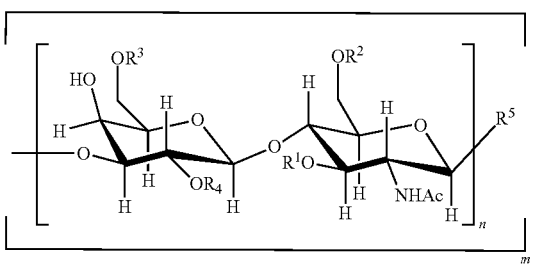

wherein Z is:

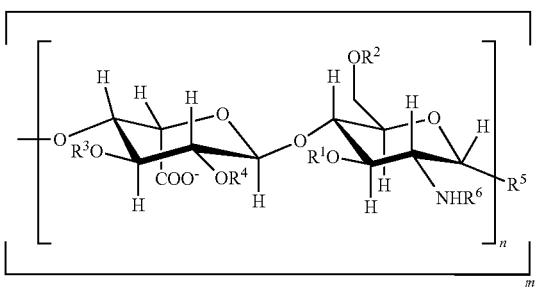

or a pharmaceutically acceptable derivative thereof,
wherein one or more of $R^1$, $R^2$, $R^3$, and $R^4$ comprises one or more sulfates;
$R^5$ is $OR7$, wherein R7 is an optionally substituted branched alkyl or alkenyl moiety; and
$R^6$ is selected from the group consisting of hydrogen, sulfate and acetyl.

Where desired, the heparan sulfate can encompass glucuronic acid based heparan, the basic structure of which is known in the art and hence not depicted herein.

Where desired, n can be selected to be 1, 10, 25, or greater, or between about 1 to about 25; m can be selected to be 5, 25, 50, 100 or greater, or between about 2-100.

In some aspects, the composition exhibits a polydispersity index less than 5, 2, or 1.5, or even less.

In some aspects, $R^1$ and $R^2$ are each independently selected from sulfate, phosphate, and carboxylate; and $R^3$ and $R^4$ are hydrogen; $R^3$ and $R^4$ are each independently selected from sulfate, phosphate, and carboxylate; and $R^1$ and $R^2$ are hydrogen; $R^1$, $R^2$, and $R^3$ are each independently selected from sulfate, phosphate, and carboxylate; and $R^4$ is hydrogen; $R^1$, $R^2$, and $R^4$ are each independently selected from sulfate, phosphate, and carboxylate; and $R^3$ is hydrogen; $R^2$, and $R^4$ are each independently selected from sulfate, phosphate, and carboxylate; and $R^1$, and $R^3$ are hydrogen; $R^1$ is selected from sulfate, phosphate, and carboxylate; and $R^2$, $R^3$, and $R^4$ are hydrogen; $R^2$ is selected from sulfate, phosphate, and carboxylate; and $R^1$, $R^3$, and $R^4$ are hydrogen; $R^3$ is selected from sulfate, phosphate, and carboxylate; and $R^1$, $R^2$, and $R^4$ are hydrogen; or $R^4$ is selected from sulfate, phosphate, and carboxylate; and $R^1$, $R^2$, and $R^3$ are hydrogen; wherein $R^5$ is $OR^7$, where $R^7$ is an optionally substituted branched alkyl or alkenyl moiety; and $R^6$ is selected from the group consisting of sulfate and acetyl.

The subject compounds may bind to growth factors, neurotrophins, axon guidance proteins, inflammatory proteins, myelin associated proteins or their corresponding cell surface receptors.

The present invention also provides a method of producing a composition comprising a population of substantially homogeneous glycosaminoglycan mimetics, comprising: subjecting a population of one or more saccharide subunits to a transition metal catalyzed ring-opening metathesis polymerization reaction under conditions to effect polymerization of individual saccharide subunits, wherein the saccharide subunit is substituted with substituted or unsubstituted cyclo-alkenyl moiety or cyclo-alkyl moiety. In one aspect, the individual members of said population of one or more saccharide subunits comprise one or more sulfates. In another aspect, one or more functional groups of said saccharide subunits comprises a protecting group that is removed after the metathesis reaction. The subject method may have a final yield of greater than 1%, 10%, 20%, 25%, 30%, 35%, 40%, 45%, 50%, 60%, 70%, 80%, 90% or even higher.

The present invention further provides a method for treating an injury or disorder comprising administering to a subject a therapeutically effective amount of a subject composition. The injury or disorder that can be treated include but are not limited to Alzheimer's Disease, Parkinson's Disease, Huntington's Disease, amyotrophic lateral sclerosis, multiple sclerosis, spinal cord injury, neuronal injury, stroke, peripheral neuropathy, osteoarthritis, phantom pain, cancer, a blood coagulation disorder, pulmonary embolism, and deep vein thrombosis.

In a related but separate embodiment, the present invention provides a method of modulating neural growth, wherein the method comprises administering an effective amount of the compound of the present invention. Where desired, the neural cell to be affected can be a brain, a stem, CNS, or peripheral neural cell. The neural cell can be a cell in a culture, including a culture of a hippocampal neuron, dopaminergic neuron, dorsal root ganglion neuron, motor neuron, or sensory neuron, or a mixture thereof.

Also provided in the present invention is a pharmaceutical composition comprising a compound of claim 1 or 4 and a pharmaceutically acceptable carrier or excipient.

Further provided in the present invention is a kit comprising a compound of the present invention together with instructions for use of said compound for inhibiting or stimulating neural growth.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 depicts the result of an experiment on the effects of glycopolymers of the present invention on neurite outgrowth.

FIG. 6 depicts an inhibition curve for inhibition of neurite outgrowth by a chondroitin sulfate glycomimetic.

DETAILED DESCRIPTION OF THE INVENTION

Definitions

Figure 1:
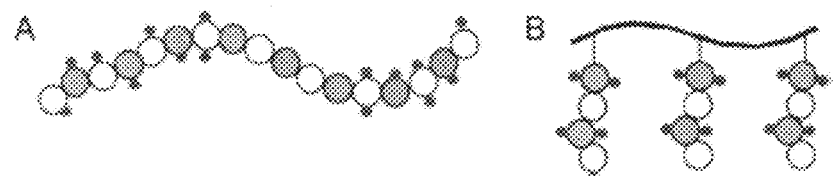
FIG. 1 is a schematic representation of a natural glycosaminoglycan and a glycomimetic of the present invention.

Abbreviations used herein have their conventional meaning within the chemical and biological arts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

As used in the specification and claims, the singular form "a", "an" and "the" include plural references unless the context clearly dictates otherwise.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. The treatment or amelioration of symptoms can be based on objective or subjective parameters; including the results of a physical examination, functional (self) evaluation, and/or any form of vision evaluation. For example, the certain methods presented herein successfully treat vision loss due to aberrant neovascularization or vascular permeability in the eye by decreasing the incidence of angiogenesis and or preventing the incidence of angiogenesis.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function of a target protein, cell or tissue. Accordingly, the terms "antagonist" and "inhibitors" are defined in the context of the biological role of the target protein, cell or tissue. A preferred biological activity inhibited by an antagonist is associated with the development, proliferation, growth, or guidance of a neuron, neurite, or axon. Another preferred biological activity inhibited by an antagonist is associated with blood coagulation. Yet another preferred biological activity inhibited by an antagonist is wound healing. Another preferred biological activity inhibited by an antagonist is associated with inflammation.

The term "agonist" as used herein refers to a compound having the ability to initiate or enhance a biological function of a target protein, cell or tissue. Accordingly, the term "agonist" is defined in the context of the biological role of the target protein, cell, or tissue. A preferred biological activity enhanced by an agonist is associated with the development, proliferation, growth, or guidance of a neuron, neurite, or axon. Another preferred biological activity enhanced by an agonist is associated with blood coagulation. Yet another preferred biological activity enhanced by an agonist is wound healing. Another preferred biological activity enhanced by an agonist is associated with inflammation.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a glycosaminoglycan, a glycomimetic, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "cell proliferation" refers to a phenomenon by which the cell number has changed as a result of division. This term also encompasses cell growth by which the cell morphology has changed (e.g., increased in size) consistent with a proliferative signal.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium (3H), iodine-125 (125I) or carbon-14 (14C). All isotopic variations of the compounds of the present invention, whether radioactive or not, are encompassed within the scope of the present invention.

"Alkyl" refers to a straight or branched hydrocarbon chain radical consisting solely of carbon and hydrogen atoms, containing no unsaturation, having from one to one hundred carbon atoms (e.g., C1-C100 alkyl). Whenever it appears herein, a numerical range such as "1 to 100" refers to each integer in the given range; e.g., "1 to 100 carbon atoms" means that the alkyl group may consist of 1 carbon atom, 2 carbon atoms, 3 carbon atoms, etc., up to and including 100 carbon atoms, although the present definition also covers the occurrence of the term "alkyl" where no numerical range is designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n propyl, 1 methylethyl (isopropyl), n butyl, n pentyl, 1,1 dimethylethyl (t butyl), 3 methylhexyl, 2 methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, ORa, —SRa, OC(O) Ra, N(Ra)2, C(O)Ra, C(O)ORa, OC(O)N(Ra)2, C(O)N(Ra)2, N(Ra)C(O)ORa, N(Ra)C(O)Ra, —N(Ra)C(O)N(Ra)2, N(Ra)C(NRa)N(Ra)2, N(Ra)S(O)tRa (where t is 1 or 2), S(O)tORa (where t is 1 or 2), S(O)tN(Ra)2 (where t is 1 or 2), or PO3(Ra)2 where each Ra is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Substituted" means that the referenced group may be substituted with one or more additional group(s) individually and independently selected from acyl, alkyl, alkylaryl, cycloalkyl, aralkyl, aryl, carbohydrate, heteroaryl, heterocyclic, hydroxy, alkoxy, aryloxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamidyl, sulfoxyl, sulfonate, and amino, including mono- and di-substituted amino groups, and the protected derivatives thereof. The substituents themselves may be substituted, for example, a cycloakyl substituent may have a halide substituted at one or more ring carbons, and the like. The protecting groups that may form the protective derivatives of the above substituents are known to those of skill in the art and may be found in references such as Greene and Wuts, above.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of a compound of the invention.

Compounds

In one embodiment, the compounds for use in the compositions and methods of the present invention have the formula I:

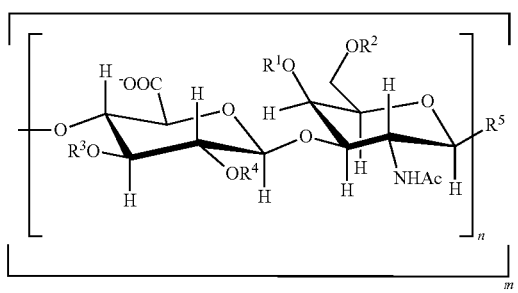

or pharmaceutically acceptable derivatives thereof, wherein $R^1$, $R^2$, $R^3$, and $R^4$ are each independently selected as follows:

(i) $R^1$ and $R^2$ are each independently selected from sulfate, phosphate and carboxylate; and $R^3$ and $R^4$ are hydrogen;

(ii) $R^3$ and $R^4$ are each independently selected from sulfate, phosphate and carboxylate; and $R^1$ and $R^2$ are hydrogen;

(iii) $R^1$, $R^2$, and $R^3$ are each independently selected from sulfate phosphate and carboxylate; and $R^4$ is hydrogen;

(iv) $R^1$, $R^2$, and $R^4$ are each independently selected from sulfate, phosphate, and carboxylate; and $R^3$ is hydrogen;

(v) $R^2$ and $R^4$ are each independently selected from sulfate, phosphate, and carboxylate; and $R^1$ and $R^3$ are hydrogen;

(vi) $R^1$ is selected from sulfate, phosphate, and carboxylate; and $R^2$, $R^3$ and $R^4$ are hydrogen;

(vii) $R^2$ is selected from sulfate, phosphate, and carboxylate; and $R^1$, $R^3$, and $R^4$ are hydrogen;

(viii) $R^3$ is selected from sulfate, phosphate and carboxylate; and $R^1$, $R^2$, and $R^4$ are hydrogen;

(ix) R4 is selected from sulfate, phosphate and carboxylate; and R1, R2, and R3 are hydrogen;

$R^5$ is $OR^7$, wherein $R^7$ is an optionally substituted branched alkyl or alkenyl moiety;

n is 1 to 100; and m is 1-100.

In some cases, n is 1-50. In another embodiment, n is 1-25. In another embodiment, n is 1-20. In another embodiment, n is 1-15. In another embodiment, n is 1-10. In another embodiment, n is 1-5. In another embodiment, n is 1-4. In another embodiment, n is 1, 2, 3, 4, 5, 6, 7, 8, 9, or 10. In another embodiment, m is 1-75. In another embodiment, m is 1-50. In another embodiment, m is about 5, 6, 7, 8, 9, 10, 12, 14, 16, 18, 20, 25, 30, 35, 40, 45, 50, 55, 60, 65, 70, 75, or about 100.

In some cases, R5 is an optionally substituted branched alkyl or alkenyl moiety. In one aspect, R5 is $OR^7$ having the formula as follows:

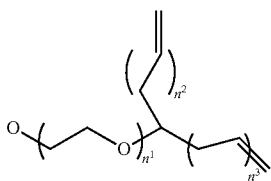

wherein $n^1$ is between 1 and 25, including 1, 2, 3, 4, 6, 7, 8, 9, 10, 11, 12, 13, 14, 15, 16, 17, 18, 19, 20, 21, 22, 23, 24, and 25, and wherein $n^2$ and $n^3$ are between 1 and 10, including 1, 2, 3, 4, 5, 6, 7, 8, 9, and 10.

Where desired, $R^5$ can be of a norbornene moiety.

In another embodiment, the compounds for use in the compositions and methods of the present invention have the formula II:

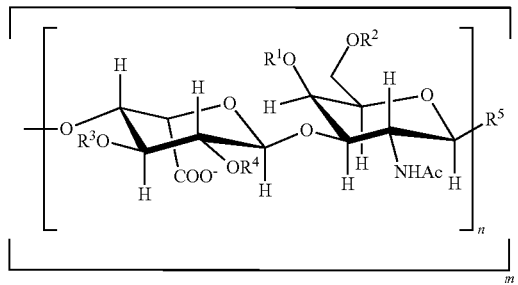

or a pharmaceutically acceptable derivative thereof, wherein the variables are as described elsewhere herein.

In another embodiment, the compounds for use in the compositions and methods of the present invention have the formula III:

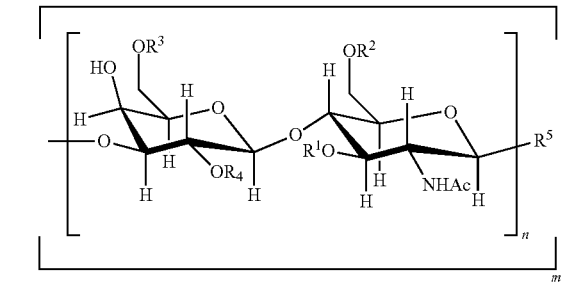

or a pharmaceutically acceptable derivative thereof, wherein the variables are as described elsewhere herein.

In another embodiment, the compounds for use in the compositions and methods of the present invention have the formula IV:

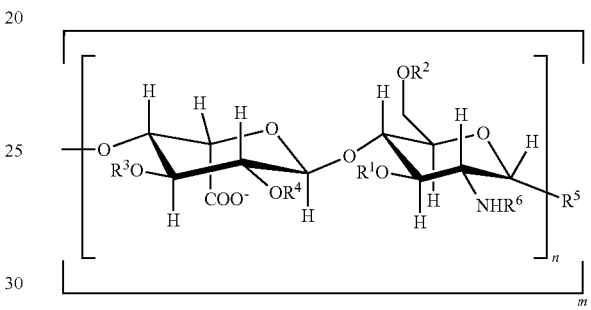

or a pharmaceutically acceptable derivative thereof, wherein $R^6$ is a sulfate, acetyl, carboxlate, or phosphate, and the variables $R^1$-$R^5$, m, and n are as described elsewhere herein.

The compounds of the present invention are glycosaminoglycan glycomimetic polymers with pendant glycosaminoglycan subunits as shown in FIG. 1 B. In FIG. 1, large circles represent monosaccharide subunits, small circles represent sulfates carboxylates, or phosphates, and the black line represents the hydrocarbon backbone of the glycopolymer. Glycosaminoglycans are long unbranched polysaccharides consisting of a repeating disaccharide unit. Members of the glycosaminoglycan family vary in the type of hexosamine, hexose or hexuronic acid unit they contain (e.g. glucuronic acid, iduronic acid, galactose, galactosamine, glucosamine). They also vary in their degree of sulfation and in their patterns of sulfation. In addition, they vary in the geometry of the glycosidic linkage. Examples of GAGs include:

| Name | Hexuronic acid/ Hexose | Hexosamine | Linkage geometry between predominant monomeric units | Unique features |
| --- | --- | --- | --- | --- |
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |

| Name | Hexuronic acid/ Hexose | Hexosamine | Linkage geometry between predominant monomeric units | Unique features |
|---|---|---|---|---|
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |
| Hyaluronan | GlcUA | GlcNAc | -4GlcUAβ1-3GlcNAcβ1- | The only GAG that is exclusively non-sulfated |

Abbreviations
GlcUA = β-D-glucuronic acid
GlcUA(2S) = 2-O-sulfo-β-D-glucuronic acid
IdoUA = α-L-iduronic acid
IdoUA(2S) = 2-O-sulfo-α-L-iduronic acid
Gal = β-D-galactose
Gal(6S) = 6-O-sulfo-β-D-galactose
GalNAc = β-D-N-acetylgalactosamine
GalNAc(4S) = β-D-N-acetylgalactosamine-4-O-sulfate
GalNAc(6S) = β-D-N-acetylgalactosamine-6-O-sulfate
GalNAc(4S,6S) = β-D-N-acetylgalactosamine-4-O, 6-O-sulfate
GlcNAc = α-D-N-acetylglucosamine
GlcNS = α-D-N-sulfoglucosamine
GlcNS(6S) = α-D-N-sulfoglucosamine-6-O-sulfate In some embodiments, the compounds have defined sulfation patterns. In some cases, the compounds of the present invention can be synthesized with defined sulfation patterns through the use of orthogonal protecting groups at the R positions, whereby the orthogonal protecting groups can be independently removed and modified (e.g. sulfated, acylated, acetylylated, phosphorylated, etc.). Suitable orthogonal protecting groups for synthesis of pendant saccharide monomer subunits include all protecting groups known in the art as well as those described herein. In some cases, the defined sulfation patterns correspond to or mimic sulfation patterns present in natural glycosaminoglycans such as chondroitin sulfate, heparan sulfate, heparin, hyaluran, dermatan sulfate, and keratin sulfate. In some cases, the degree and pattern of sulfation may be tuned to alter the biophysical, or biochemical activity of the glycopolymers. For example, compounds may be tuned to inhibit or stimulate growth of cells such as neural cells or tumor cells. In some embodiments, the pendant saccharides of the multivalent glycopolymers of the present invention may be capped with fucose moieties.

Preparation of Compounds

Figure 2:
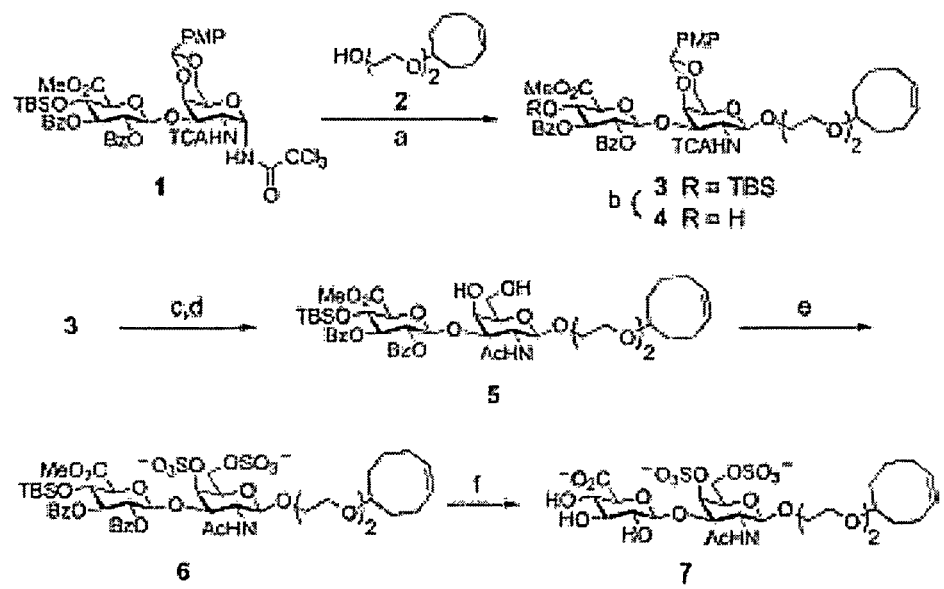
FIG. 2 is a synthetic scheme for synthesis of glycomimetic pendant saccharides with defined sulfation.

The compounds of the present invention may be synthesized by a number of methods. Individual pendant saccharide subunits may be synthesized as shown in FIG. 2 or by any of the methods described in U.S. Patent Application No. PCT/US05/18906. As shown in FIG. 2, various glycosaminoglycan molecules can be accessed from a single disaccharide building block, such as for example compound 1. The use of a p-methoxybenzylidene acetal protecting group for the hydroxyl groups that are to be sulfated allows for their selective sulfation. The use of a tert-butyldimethylsilyl protecting group at the C-4 position on the non-reducing end of compound 1 facilitates the synthesis of longer saccharide monomer subunits. To achieve stereo-selective formation of glycosidic linkages, N-trichloroacetyl and benzoyl protecting groups are used (Coutant, C.; Jacquinet, J. C. *J. Chem. Soc.—Perkin Trans.* 11995, 1573-1581). Finally, the anomeric hydroxyl of the pendant subunits is masked with an optionally substituted cyclo-alkyl moiety with at least one carbon-carbon double bond as in compound 5.

The use of the optionally substituted cyclo-alkyl group with at least one carbon-carbon double bond allows the subsequent use of ring-opening metathesis polymerization or "ROMP" to afford the multivalent glycomimetic glycopolymers of the present invention in good yield, with a substantial degree of polymerization (i.e. m between about 1 and about 100 or even more), and a relatively narrow polydispersity index (i.e. between about 5 and about 1).

ROMP is a variant of the olefin metathesis reaction and uses optionally substituted cyclic alkyls with at least one carbon-carbon double bond to produce polymers and co-polymers with a low polydispersity index. The mechanism of the ROMP reaction and is identical to the mechanism of olefin metathesis. The catalysts used in the ROMP reaction include a wide variety of metals, particularly transition metals (e.g. ruthenium, molybdenum, or tungsten) and range from a simple ruthenium trichloride/alcohol mixture to Grubbs' catalyst or derivatives thereof. In some embodiments, the ROMP reaction requires a strained cyclic structure to drive the reaction by release of ring strain. Suitable strained cyclic structures include but are not limited to cyclobutene, cyclopentene, norbornene, bi and tri-cyclic rings, cyclooctene, and derivatives thereof. Additional suitable cyclo-alkyl rings for use in ROMP are described herein. In some embodiments, various substituents can be included in the cyclo-alkyl ring, in the transition metal catalyst, or in the reaction mixture to tune the polymerization reaction. Substituents suitable for tuning the polymerization reaction include any known organic and inorganic moieties including but not limited to alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, ORa, —SRa, OC(O)Ra, N(Ra)2, C(O)Ra, C(O)ORa, OC(O)N(Ra)2, C(O)N(Ra)2, N(Ra)C(O)ORa, N(Ra)C(O)Ra, —N(Ra)C(O)N(Ra)2, N(Ra)C(NRa)N(Ra)2, N(Ra)S(O)tRa (where t is 1 or 2), S(O)tORa (where t is 1 or 2), S(O)tN(Ra)$_2$ (where t is 1 or 2), or PO3(Ra)2 where each Ra is independently hydrogen, alkyl, fluoroalkyl, carbocyclyl, carbocyclylalkyl, aryl, aralkyl, heterocyclyl, heterocyclylalkyl, heteroaryl or heteroarylalkyl.

In one embodiment, the $R^5$ position of the saccharide subunits of the present invention prior to polymerization by ROMP is a cylco-alkyl or cyclo-alkenyl moiety. In one aspect, $R^5$ is $OR^7$ having the formula:

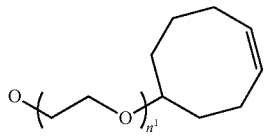

wherein $n^1$ is between 1 and 25, including 1, 2, 3, 4, 6, 7, 8, 9, 10, 11, 12, 13, 14, 15, 16, 17, 18, 19, 20, 21, 22, 23, 24, and 25. In another embodiment, $n^1$ is between 25 and 100, including about 25, 30, 35, 40, 45, 50, 60, 70, 80, 90 or about 100. In yet another embodiment, R5 is an optionally substituted cycloalkenyl such as a cyclooctane, cycloheptane, cyclohexane, or cyclopentane. In still other embodiments, R5 is any optionally substituted alkyl ring with at least one carbon-carbon double bond. The compounds and methods of the present invention are not limited in the precise position of the carbon-carbon double bond and as such the double bond may be at any position within the ring.

The synthesis of the compounds of the present invention is illustrated in FIG. 2. The disaccharide 1, may be synthesized from monosaccharide subunits derived from commercially available precursors such as for example p-tolyl-1-thio-β-D-glucopyranose (Clingman, A. L.; Richtmyer, N. K. *J. Org. Chem.* 1964, 29, 1782-1787) and 1,3,4,6-tetra-O-acetyl-2-azido-2-deoxy-D-galactopyranose (Lemieux. R. U.; Ratcliffe, R. M. *Can. J. Chem.—Rev. Can. Chim.* 1979, 57, 1244-1251). Coupling of the monosaccharide subunits can be performed using the trichloroacetimidate procedure (Schmidt, R. R.; Kinzy, W. *Adv. Carbohydr. Chem. Biochem.*, 1994, Vol. 50. 21-123).

To obtain compounds 6 and 7 of FIG. 2, the trichloroacetimidate donor 1, can be coupled to the cyclooctene acceptor 2 to afford exclusively the β-linked disaccharide 3 in 69% yield. Removal of the tert-butyldimethylsilyl group using HF-pyridine gives 4, which serves as a glycosyl acceptor to assemble tetrasaccharides as outlined in FIG. 3. Free radical reduction of the trichloroacetyl group and DDQ oxidation of the p-methoxybenzylidene acetal of 3 provides diol 5, in 82% yield, which gives 6 upon sulfation with sulfur trioxide-trimethylamine complex. Alternatively, desilylation followed by saponification using a sequential LiOOH—NaOH treatment to minimize β-elimination at the C4 position provides deprotected disaccharide subunit 7. Other disaccharide subunits of the present invention may be synthesized in a similar manner using for example glucose, glucuronic acid and iduronic acid precursors.

ROMP is typically performed in non-coordinating aprotic solvents. However, in some cases the compounds of the present invention are substantially insoluble in non-polar solvents. Therefore, in some cases, the pendant saccharide subunits may be polymerized by ROMP in a polar protic solvent such as MeOH, EtOH, isopropanol, water, or any polar protic solvent known in the art. Polymerization of 7 in MeOH using 2.5 mol % of the fast-initiating catalyst $(H_2IMes)(Py)_2(Cl)_2Ru=CHPh$ (8) provides incomplete conversion (36%) to glycopolymer 9 with a low degree of polymerization (DP=21). Similarly, ROMP of 7 in aqueous solution using 2.5 or 5 mol % of the water soluble catalyst $H_2Imes$-poly(ethyleneglycol)) $(Cl)_2Ru=CH(o-iPrOC_6H_4)$ provides incomplete conversion (7 or 60% respectively) and low molecular weight polymers (DP=8 or 28 respectively).

Figure 3:
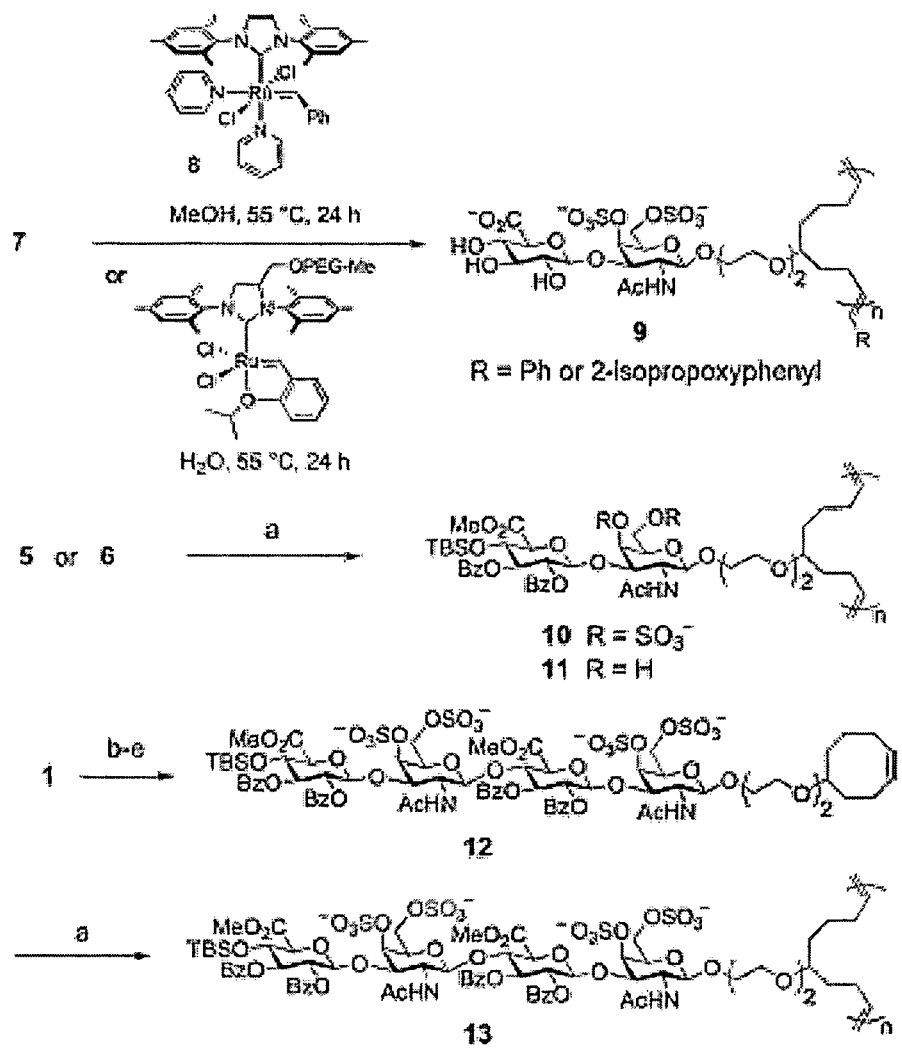
FIG. 3 is a synthetic scheme for synthesis of multivalent glycomimetic glycopolymers with defined sulfation.

In order to provide higher rates of conversion and more robust polymerization, pendant saccharide subunits can be polymerized by ROMP in cosolvent mixtures that contain a lower ratio of polar protic solvent than the solvent systems described above. For example, a $MeOH/(CH_2Cl)_2$ cosolvent mixture may be used in the methods of the present invention. Various ratios of solvent and cosolvent may be used to support ROMP in the methods of the present invention. One skilled in the art will readily be able to determine appropriate solvent/cosolvent mixtures based on principles of solubility of starting compound and catalyst, and the likelihood of inhibition of the reaction by coordination of the solvent to the catalyst and the reactive intermediates. Exemplary solvent/cosolvent mixtures include $MeOH/CH_4Cl_2$ at about a 1:5 ratio, 1:1 ratio, 1:2 ratio, 1:4 ratio, and about a 1:10 ratio. As depicted in FIG. 3 reaction of compound 6 in a 1:5 MeOH/$CH_4Cl_2$ cosolvent with catalyst 8 at 55° C. affords substantially complete conversion to glycopolymer 10 with 40 repeating units. Examples of the results of other polymerization attempts are provided herein:

| entry | monomer | mol % catalyst | polymer | % yield | n (DP) | Mn (g/mol) | PDI |
|---|---|---|---|---|---|---|---|
| 1 | 6 | 5.0 | 10 | 88 | 25 | 28 320 | 1.63 |
| 2 | 6 | 2.5 | 10 | 59 | 40 | 43 780 | 1.34 |
| 3 | 6 | 1.0 | 10 | 55 | 58 | 63 400 | 1.35 |
| 4 | 6 | 0.5 | 10 | 53 | 80 | 87 540 | 1.24 |
| 5 | 5 | 2.5 | 11 | 69 | 39 | 36 100 | 1.61 |
| 6 | 12 | 2.0 | 13 | 51 | 64 | 119 000 | 1.33 |

In some embodiments of the present invention, the molecular weight and/or degree of polymerization (DP) of the pendant multivalent glycomimetic polymers of the present invention may be controlled by varying the conditions under which ROMP is performed. For example, the degree of polymerization may be controlled by using varying amounts of catalyst from 0.1% to yield low degrees of polymerization to 5 or even 10 mol % or higher to yield high degrees of polymerization. In other cases, the time or temperature or cosolvent system may be varied to achieve different degrees of polymerization.

In some embodiments of the present invention the synthetic methods as described herein provide glycopolymers with relatively narrow polydispersities. A relatively narrow polydispersity (e.g. less than about 5, less than about 4, less than about 3, less than about 2, less than about 1.7, less than about 1.5, or less than about 1.3) is advantageous because glycopolymers of different degrees of polymerization may have different biological effects. By way of example only, a glycopolymer of DP 5 may promote neurite outgrowth, while a glycopolymer of DP 100 may inhibit neurite outgrowth. While both compounds may be useful, it may also be beneficial to use the methods of the present invention to selectively synthesize a population that substantially consists of glycopolymers of one DP or another without substantial contamination with glycopolymers of the other DP. Therefore, methods such as those of the present invention that lead to glycopolymers with a relatively narrow polydispersity provide for the synthesis of populations of glycopolymer that are substantially free of interfering glycopolymers with differing DP and thus differing biological effects. In some cases, polydispersity or a polydispersity index can be calculated by determining the weight averaged molecular weight of a population of compounds and the number averaged molecular weight of a population of compounds and dividing the weight averaged molecular weight by the number averaged molecular weight. As a sample population approaches a single pure species at a defined molecular weight, the polydispersity index approaches an ideal value of 1. Experimental means for determining the polydispersity index of a compound include mass spectrometry, gel permeation chromatography, and light scattering.

In some embodiments of the present invention, the synthetic methods described herein provide glycopolymers with substantial homogeneity after synthesis, work-up and purification. Methods for purifying final product compounds include any standard methods known in the art. Exemplary methods include but are not limited to thin layer chromatography; silica gel, reverse phase, ion-exchange, and gel permeation chromatography; and lypholization. As used herein, substantial homogeneity means at least about 25% pure including about 30%, 35%, 40%, 45%, 50%, 55%, 60%, 65%, 70%, 75%, 80%, 85%, 90%, 95%, 97.5%, 99%, or about 99.5% pure or higher. In some embodiments, substantially homogeneous may additionally mean having a polydispersity index of less than about 5, less than about 4, less than about 3, less than about 2 or less than about 1.5. Means for calculating purity include but are not limited to chromatographic methods including the use of refractive index and electrochemical detection. Methods for calculating purity further include light scattering, mass spectrometry, and sedimentation velocity. In some cases, a chromophore or fluorophore may be covalently linked to the compounds of the present invention allowing detection by spectrophotometric (UV/Vis) or fluorometric means.

In some embodiments of the present invention, the methods described herein provide glycopolymers in high yield. Synthetic yields may be calculated by any standard means known in the art. Exemplary means include determining the amount and purity of starting material and determining the amount and purity of final product, dividing final product by starting material and multiplying by 100 to obtain a percent yield. In determining the yield, one may further take into consideration the stoichiometry of the reaction. By way of example only, if the starting material includes 1 millimol of galactosamine which is incorporated into a tetrasaccharide pendant subunit (i.e. n=4) which is further incorporated into a glycopolymer of 10 repeating units (i.e. m=10), then a 100% yield would provide 0.05 millimol of final product which corresponds to the incorporation of 1 millimol of galactosamine. Methods for determining the amount of starting material and/or final product include but are not limited to weighing. In some cases, the final yield may be determined by multiplying the yield at each step of the synthetic scheme. In some embodiments, the methods of the present invention provide multivalent pendant saccharide glycopolymer glycomimetics at yields of between about 1% and 50% including about 1%, 2%, 3%, 4%, 5%, 7.5%, 10%, 15%, 20%, 25%, 30%, 35%, 40%, and about 50% based on the amount of starting material.

Figure 4:
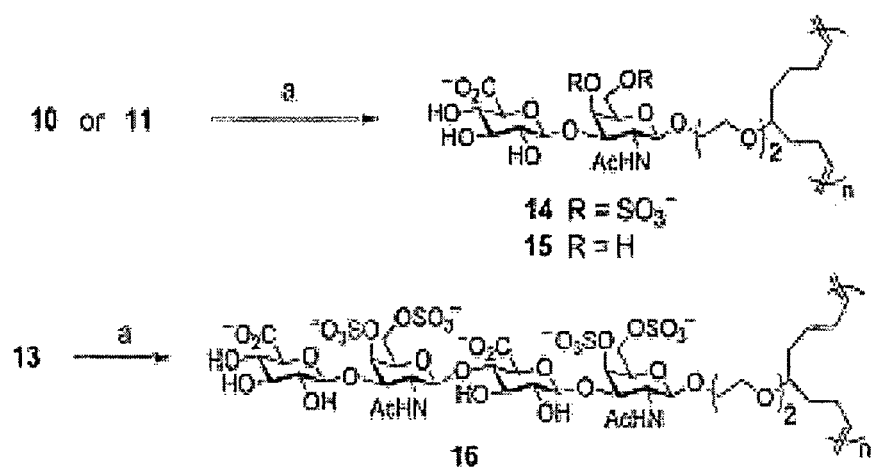
FIG. 4 is a synthetic scheme for synthesis of multivalent glycomimetic glycopolymers with a different defined sulfation pattern.

In some embodiments of the present invention, multivalent chondroitin sulfate glycomimetic glycopolymers may be synthesized as in FIG. 4 by desilylation and sequential LiOOH—NaOH treatment in 87-95% yield in two steps to afford compounds 14-16. In some embodiments of the present invention, the methods of the present invention may be used to synthesize multivalent pendant saccharide glycomimetic glycopolymers corresponding to any naturally occurring or non-naturally occurring isoforms of the glycosaminoglycans. For example, the methods of the present invention provide for synthesizing chondroitin sulfate isoforms A, C, and E.

In some embodiments of the present invention, pendant saccharide subunits of different composition and or sulfation may be combined via ROMP to generate chimeric multivalent glycomimetic glycopolymers. For example disaccharide subunits corresponding to chondroitin sulfate A, C, and E may be combined and polymerized, or a mixture of tetrasaccharide subunits corresponding to chondroitin sulfate A, C, and E may be combined and polymerized, or a mixture of di and tetrasaccharides may be combined and polymerized, or a mixture of chondroitin sulfate and keratan sulfate saccharides may be combined and polymerized, or a mixture of keratan and dermatan sulfate saccharides may be combined and polymerized to generate multivalent glycomimetic glycopolymers. It is understood that essentially any possible combination of disaccharide and larger subunits of any degree of sulfation may be combined and polymerized to generate glycomimetics of the present invention.

Block co-polymers containing defined, alternating regions of CS sulfation (e.g., CS-E block followed by CS-D block) can be synthesized from the corresponding norbonene building blocks using ROMP chemistry with Grubbs' second generation catalyst. PDI values less than 1.5 were obtained for such polymers. In addition, heparin/heparan sulfate-based polymers can be synthesized from both cyclooctene- and norbonene-containing heparin disaccharides to generate glycopolymers according to the general scheme described herein.

Formulation of Pharmaceutical Compositions

The invention provides a pharmaceutical composition comprising one or more compounds disclosed herein. In some embodiments the invention provides pharmaceutical compositions for the treatment of disorders in a mammal such as hyperproliferative disorders, neuro-degenerative disorders, inflammatory disorders, and coagulation disorders. In some embodiments, the treatment of said disorders comprises a therapeutically effective amount of a compound of the present invention, or a pharmaceutically acceptable salt, ester, prodrug, solvate, hydrate or derivative thereof, and a pharmaceutically acceptable carrier. In some embodiments, the invention also relates to compositions for the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to compositions for the treatment of neuronal injuries in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to compositions for the treatment of pain such as for example phantom pain disorder in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to a composition for treating a disease related to vasculogenesis or angiogenesis in a mammal. In some embodiments, the invention relates to pharmaceutical compositions for treating a disease related to vasculogenesis or angiogenesis in a mammal which comprises a therapeutically effective amount of a compound of the present invention, or a pharmaceutically acceptable salt, ester, prodrug, solvate, hydrate or derivative thereof, and a pharmaceutically acceptable carrier. In some embodiments, said pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, the invention provides a composition that contains a compound of the present invention. In some embodiments, the concentration of one or more of the compounds is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

The compounds of the present invention may be administered in the form of pharmaceutical compositions. The other agents described herein are also administered in the form of pharmaceutical compositions. When the compounds of the present invention are used in combination with other agents, both components may be mixed into a preparation or both components may be formulated into separate preparations to use them in combination separately or at the same time.

This invention therefore provides pharmaceutical compositions that contain, as the active ingredient, a compound of the present invention or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

This invention further provides pharmaceutical compositions that contain, as the active ingredient, a compound of the present invention or a pharmaceutically acceptable salt and/or coordination complex thereof, a second agent or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The compound of the present invention may be prepared into pharmaceutical compositions in dosages as described herein (see, e.g., Compositions). Such compositions are prepared in a manner well known in the pharmaceutical art.

Pharmaceutical Compositions for Oral Administration

In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoylactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glycerylaurate, PEG-30 glycerylaurate, PEG-20 glyceryl stearate, PEG-20 glyceryl oleate, PEG-30 glyceryl oleate, PEG-30 glycerylaurate, PEG-40 glycerylaurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the invention provides pharmaceutical compositions for transdermal delivery containing a compound of the present invention and a pharmaceutical excipient suitable for transdermal delivery. In other cases, such as for example for treatment of psoriasis or a rash, the invention provides pharmaceutical compositions for topical administration to the skin for treatment at or near the site of administration.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkenes, water, calcium carbonate, calcium phosphate, various sugars, starches, cellulose derivatives, gelatin, and polymers such as polyethylene glycols.

Another preferred formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, intraspinal, or intracranial administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Evaluation of the Activity of the Compounds

The activity of the compounds provided herein can be assessed by methods and assays known to one skilled in the art. For example, the biological activity can be assessed in assays known for testing the activity of chondroitin sulfate, keratan sulfate, heparin, dermatan sulfate, or heparan sulfate.

In some embodiments, the activity of the compounds provided herein to modulate neuronal growth can be tested using for example cultured primary hippocampal neurons, dopaminergic neurons, or dorsal root ganglion neurons. Primary hippocampal neurons can be cultured on a suitable substrate, such as for example poly-DL-ornithine or poly-D-lysine coated coverslips with or without each compound of the present invention. After a suitable period of time such as for example 8 to 96 hours including about 8, 10, 12, 16, 20, 24, 36, 48, 72, and about 96 hours, neurons may be fixed, immunostained with an antibody that stains neurons such as for example anti-tau antibodies, and examined by for example confocal fluorescence microscopy.

In some embodiments, the activity of the compounds provided herein to modulate neuronal outgrowth can be tested either in solution or on a substrate. For example polyDL-ornithine plates or other suitable substrate may be coated with the compounds of the present invention as described above, alternatively the compounds of the present invention may be added to the solution (e.g. the media) surrounding the cells. In some cases, the method of applying the compound of the present invention (i.e. in solution or on the substrate) affects the way in which the cell growth is modulated. For example, glycosaminoglycan glycomimetics on the substrate may recruit growth factors and thereby stimulate downstream signaling pathways involved in neuronal growth. In contrast, by adding a glycosaminoglycan mimetic to the solution in which the neurons are present, growth factors may, for example, be sequestered away from the cell surface resulting in neurite inhibition.

The effect of a multivalent glycopolymer based on the sulfated chondroitin sulfate isoform chondroitin sulfate E (i.e. compounds 14-16) can be seen in FIG. 5. compound 14 which has a repeating disaccharide chondroitin sulfate isoform E subunit robustly inhibits neurite outgrowth to a similar extent as the natural polysaccharide. In contrast, the chondrotin sulfate isoform E disaccharide itself (7) has no effect on neurite outgrowth. In some cases, the degree of polymerization (i.e. the valence) of the glycopolymers affects the activity of the glycopolymer. For example, (14) was tested at a DP of 25, 40, 58, and 80 and showed an increasing biological effect at higher DP. In some cases, the degree and/or pattern of sulfation affects the activity of the glycopolymer. For example, compound 15 which is unsulfated has substantially no effect on neurite growth at the concentrations tested. In some cases, the multivalency of the glycopolymers of the present invention provides for enhanced biological activity as compared to the biological activity of the pendant saccharide subunit. For example, the chondroitin sulfate isoform E tetrasaccharide has been shown to have a small neurite growth promoting activity when applied on a substratum to a neuron, and a small neurite growth inhibiting activity when applied to the solution surrounding a neuron. In contrast, the multivalent chondroitin sulfate isoform E tetrasaccharide compound 16 exhibits potent inhibition of neurite growth when tested in solution FIGS. 5 and 6. Alternatively, the multivalent glycopolymer can be used to affect the growth cones in sensory neuron explants. In one aspect, the multivalent glycopolymer is effective in collapsing growth of these explants.

In some embodiments, the compounds may be tested to determine an effective or an inhibitory concentration. In some embodiments, the compounds may be tested to determine a concentration at which a biological effect is modulated by a specified percentage relative to a control or a normal protein cell or tissue. For example, the compounds provided herein may be contacted with neuronal cells at varying concentrations to determine at what concentration outgrowth of neurites or axons is affected (e.g. enhanced or inhibited) by a specified percentage such as for example 40%, 50%, 60%, 70%, 80%, 90%, 95%, 97.5%, 99%, or 99.5%. Such a concentration is termed the effective concentration or the EC. The EC may further include the specified percentage. For example an EC50 is the concentration at which a biological effect is modulated (e.g. enhanced or inhibited) by 50% by a compound. Similarly an IC50 is the concentration at which a biological effect is inhibited by a compound.

In another embodiment of the present invention, compounds may be tested for their ability to bind proteins known to be or suspected of being involved in interactions with naturally occurring glycosaminoglycans. For example, the compounds may be tested for their concentration dependent binding to proteins such as tumor necrosis factor α, and midkine. Other exemplary proteins that bind glycosaminoglycans are provided in the following table:

| Class | Examples | Physiological/pathophysiological effects of binding |
|---|---|---|
| Enzymes | glycosaminoglycan biosynthetic enzymes, thrombin and coagulation factors (proteases), complement proteins (esterases), extracellular superoxide dismutase, topoisomerase | multiple |
| Enzyme inhibitors | antithrombin III, heparin cofactor II, secretory leukocyte proteinase inhibitor, C1-esterase inhibitor | coagulation, inflammation, complement regulation |
| Cell adhesion proteins | P-selectin, L-selectin, some integrins | cell adhesion, inflammation, metastasis |
| Extracellular matrix proteins | laminin, fibronectin, collagens, thrombospondin, vitronectin, tenascin | cell adhesion, matrix organization |
| Chemokines | platelet factor IV, γ-interferon, interleukins | chemotaxis, signaling, inflammation |
| Growth factors | fibroblast growth factors, hepatocyte growth factor, vascular endothelial growth factor, insulin-like growth factor-binding proteins, TGF-β-binding proteins | mitogenesis, cell migration |
| Morphogens | hedgehogs, TGF-β family members | cell specification, tissue differentiation, development |
| Tyrosine-kinase growth factor receptors | fibroblast growth factor receptors, vascular endothelium growth factor receptor | mitogenesis |
| Lipid-binding proteins | apolipoproteins E and B, lipoprotein lipase, hepatic lipase, annexins | lipid metabolism, cell membrane functions |
| Plaque proteins | prion proteins, amyloid protein | plaque formation |
| Nuclear proteins | histones, transcription factors | unknown |
| Pathogen surface proteins | malaria cirumsporozoite protein | pathogen infections |
| Viral envelope proteins | herpes simplex virus, dengue virus, human immunodeficiency virus, hepatitis C virus | viral infections |

Methods for ascertaining binding include any methods known in the art such as chromatographic methods, bead-based methods, methods based on fluorescence, or UV-Vis spectroscopy, colorimetric methods, ultracentrifugation, light scattering, cross-linking studies, immunoaffinity pull-downs, magnetic separation, and equilibrium dialysis. In some cases, such as for example, immunoaffinity pull-downs and bead-based methods, the interaction between the compounds of the present invention and one or more proteins may be detected by western blot.

To determine the physiological relevance of the interaction, one may in some cases consider measuring binding under conditions that can lead to a biological response. For example, one can measure binding to cells with altered glycosaminoglycan composition or after treatment with specific lyases to remove glycosaminoglycan chains from the cell surface and then determine whether the same response occurs as that in the presence of the glycosaminoglycan chains. The interaction can then be studied more intensively using the in vitro assays described above.

Methods of Using the Compounds of the Present Invention

The compounds of the present invention are useful for study and/or treatment of a number of diseases and conditions. In some embodiments, the compounds of the present invention are useful for the study of the patterning and/or growth of neurons, including neuronal cells from the CNS, brain, spinal cord, and peripheral nerves. In other embodiments, the compounds of the present invention are useful for the treatment of neurodegenerative diseases, neural development disorders, or injuries to neural tissues such as brain or spinal cord injuries. The methods of the present invention include contacting a neuronal cell, or an injured or severed nerve with a compound provided herein in an amount effective to modulate neuronal outgrowth. The method may be performed in vitro or in vivo.

In certain embodiments, the compounds of the present invention are used in the in vitro study of neuronal growth. Any variety of mammalian neuronal cells, including those from the brain, CNS, peripheral nerves and the like can be treated by the methods provided herein. In addition, the cells may be from any variety of mammalian species including human, mouse, rat, and any other mammalian species such as agricultural stock or non-domesticated animals.

In some cases, non-mammalian neuronal cells may be used to screen for compounds which affect neurite outgrowth, axon guidance, and/or neural cell viability. For example, teleosts may be used to study the effect of the compounds. The use of teleosts in the methods of the present invention to study neurite outgrowth has several advantages due to their small size, rapid development, ease of genetic and embryological manipulation, and transparency. The compounds of the present invention can be applied to teleosts topically, by injection, or in the liquid medium. The compounds can be applied to eggs, embryos, or adult teleosts. In some cases, the results of studies in teleosts may form the basis of future studies in mammalian or human subjects. In other cases, the methods of the present invention provide for the study of the compounds of the present invention in avian subjects such as but not limited to the use of a chicken embryo animal model.

In some cases, the compounds are used to induce neuronal growth in cultured neurons, including but not limited to hippocampal neurons, dopaminergic neurons, motor neurons, sensory neurons, and dorsal root ganglion neurons. In certain embodiments, the compounds provided herein are useful for inducing the growth of differentiated neural stem cells prior to implantation. In the case of Parkinson's disease, for instance implanted tissue has promise as a replacement for dying dopaminergic neurons.

In some embodiments, the compounds of the present invention may affect axon guidance, nuerite outgrowth, neural proliferation, and/or neural cell viability. As neurons begin to assemble into recognizable structures, they can begin to extend elongated membrane-enclosed protrusions of cytoplasm that are called processes or neurites. Many of these neurites will eventually mature into dendrites or axons. These neurites grow toward tissues such as other regions of the nervous system or other structures on which the neurons will eventually form synapses or junctions with other tissues such as muscles or glands. These tissues are often referred to as targets of the neurons, and proper function of the nervous system depends on the proper connections between the neurons and their targets. In some cases, neurite outgrowth is guided by interaction between the neurons and molecules on the surface of cells or in the extracellular matrix of the tissues through which they grow. These physical interactions attract axons and neurites to grow in certain directions and avoid growing in other directions. In addition, there are diffusible molecules that are similarly attractive or repellent to neurite and/or axon growth.

Molecules that attract or repel neurite and/or axon growth include but are not limited to integrins, cadherins, IN-1, laminins, netrins, semaphorins, ephrins, BMPs, Wnts, hedgehog, FGFs, tenascins, proteoglycans, neurotransmitters, nerve growth factor, NCAM, L1, Slit proteins, fibronextin, Comm, Robo, DCC, Robo, Nogo, paxilin, retinoic acid, and glycosaminoglycans. Additionally, there are many known inhibitors or stimulators of neurite outgrowth that can be used to study neuronal patterning. Such compounds include but are not limited to Bis-I, K252a, okadaic acid, U0126, methylmurcery, desamethasone, amphetamine, and vincristine. In some cases, anti-proliferative compounds or neurotoxicants such as for example kinase inhibitors, inhibitors of tubulin polymerization, inhibitors of nucleic acid synthesis, inhibitors of metabolic pathways, cell cycle inhibitors, diphenhydramine, cadmium, lead, 5,5-diphenylhydantoin, and valproic acid can be used to inhibit neurite outgrowth, neuron proliferation, and/or neuron viability. Other antiproliferative compounds known to affect neural cell proliferation and/or viability include but are not limited to aphidicolin, hydroxyurea, cytosine arabinoside, 5-fluorouracil, and ochratoxin A.

The compounds of the present invention may be assayed individually for their effects on neurite outgrowth, neuron proliferation, and/or neuron viability, or they may be assayed in combination with other glycomimetics of the present invention or in combination with other compounds known or suspected to affect neurons. The compounds may be tested for their ability to augment and/or mitigate the effect of other compounds on neurons. In some cases, the compounds provided herein are administered in combination with tumor necrosis factor α (TNF-α), and/or nerve growth factor (NGF). In some cases, the compounds provided herein interact with growth factors and cytokines such as but not limited to TNF-α, FGF, and NGF. In some cases, the compounds provided herein may be tested relative to one or more controls. Controls include cells not contacted with the compounds of the present invention, or cells contacted with other compounds. In some cases, controls may be a value understood to be normal, that is not inhibited or enhanced. For example, neurons under the conditions tested may be known to exhibit neurite outgrowth to a specified degree or length. The compounds may be tested for their ability to induce or inhibit neurite outgrowth relative to that specified degree or length (i.e. relative to the control).

In some embodiments of the present invention, the compounds provided herein are screened for their ability to induce neurite outgrowth. The methods involve contacting a cultured neuron with a compound bearing one or more negatively charged groups (e.g. sulfates) and determining the increase in neurite length of a treated versus untreated control. In some cases, a compound of the present invention may inhibit neurite outgrowth when applied in solution to the neurons, but may induce neurite outgrowth when applied to a substratum as described previously. In some cases, the methods and compounds of the present invention cause an increase in mean neurite length relative to an untreated cell between about 1% and about 50%. In other cases, the increase in mean neurite length is greater than about 1%, about 2%, about 5%, about 10%, about 15%, about 20%, about 25%, about 30%, about 35%, about 40%, about 45%, or greater than about 50%. In other cases, the increase in mean neurite length is greater than 10%, 20%, or 30% relative to an untreated cell.

In other embodiments, the compounds may be screened against neurons that exhibit various disease phenotypes. For example, superoxide dismutase or SOD1 mutant neurons develop an amyotrophic lateral sclerosis (ALS)-like phenotype. The compounds may contacted with SOD1 mutant neurons and tested for their ability to inhibit the development of ALS. Similarly, the compounds may be tested against suitable model systems for Huntington's Disease, Parkinson's Disease, and Alzheimer's disease or any other neurodegenerative disease known in the art including but not limited to Alexander's disease, Alper's disease, ataxia telangiectasia, Batten disease, bovine spongiform encephalopathy, Canavan disease, Cockayne syndrome, corticobasal degeneration, Creutzfeldt-Jakob disease, HIV-associated dementia, Kennedy's disease, Krabbe's disease, lewy body dementia, Machado-Joseph disease, multiple sclerosis, multiple system atrophy, narcolepsy, neuroborreliosis, Pelizaeus-Merzbacher Disease, peripheral neuropathy, Pick's disease, primary lateral sclerosis, prion diseases, Refsum's disease, Sandhoff's disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes dorsalis.

In some embodiments, the compounds of the present invention may be useful for the study and/or treatment of other diseases or conditions such as but not limited to osteoarthritis, spinal cord injury, neuronal injury, cancer, blood coagulation diseases or conditions, and deep vein thrombosis. It is known in the art that growth factors involved in cancers interact with glycosaminoglycans such as but not limited to chondroitin and heparan sulfate. The methods of the present invention provide for the use of the compounds provided herein for modulation of cancer growth and/or progression.

Examples of cancers whose growth and/or proliferation may be modulated by the methods and compounds of the present invention breast cancer include but are not limited to ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments of the present invention glycomimetics of hyaluronic acid and/or chondroitin sulfate inhibit TNF-α and thus reduce inflammation. In some cases, this reduction in inflammation by administration of compounds of the present invention may be useful for the treatment of inflammatory diseases including but not limited to chronic inflammatory disease such as arthritis, rheumatoid arthritis, atherosclerosis, and inflammatory bowel disease. Methods for assaying the effect of the compounds of the present invention on inflammation include but are not limited to a leukocyte adhesion assay, an NF-κB activation assay, a cytokine release assay, an elastase or tryptase release assay, a reactive oxygen species production and a reactive nitrogen species production assay.

In some embodiments, the compounds of the present invention may be useful for the enhancement of wound repair.

Various glycosaminoglycans such as for example chondroitin sulfate, heparan sulfate, and dermatan sulfate are implicated in wound repair. The compounds of the present invention may be used as glycomimetics of the naturally occurring glycosaminoglycans to enhance wound repair. Compounds of the present invention may be applied topically to a wound or integrated into a bandage or suture material. Methods for assaying wound healing include but are not limited to the scratch assay, the assay described in Rodriguez et al. *Methods Mol Biol.* 2005; 294:23-9, and the rodent ear-punch assay.

Kits

Kits of the present invention are provided herein. In some cases, the kit includes one or more compounds of the present invention in a suitable container. The kit may in some cases further contain suitable solvents and/or excipients for administering the compound to a cell or a subject. The kit may also contain instructions for the use of the kit such as for example, methods of administering the one or more compounds, methods of using the one or more compounds for screening for a biological effect (e.g. neurite outgrowth, inflammation, wound healing, blood coagulation etc.), and methods of using the one or more compounds for treating a disease or condition. In some cases, the kit may contain cells suitable for screening or administering to a subject. For example, the kit may contain neurons such as hippocampal neurons for screening or dopaminergic neurons for administration to a subject suffering from Parkinson's disease. In some cases, the kit may further contain media or media components and/or suitable containers for culturing the cells such as petri dishes, assay plates, flasks, slides, or cover slips. In some cases, the petri dishes, assay plates, flasks, slides, or cover slips may be coated on one or more surfaces with compounds of the present invention or other components such as for example collagen, laminin, or extracellular matrix components. A kit typically contains instructions for user to use the contents contained in the kit.

EXAMPLES

Example 1

In Vitro Assay for Effects of Compounds on Neurite Outgrowth

We evaluated the biological activity of the glycopolymers by measuring their ability to modulate the outgrowth of hippocampal neurons. Neurons were cultured on poly-DL-ornithine-coated glass coverslips, and each glycopolymer was added in solution to the neurons. After 48 h, the neurons were fixed, immunostained with anti-tubulin antibodies, and examined by fluorescence microscopy. We found that natural polysaccharides enriched in the chondroitin sulfate (CS) isoform E (CS-E) sulfation motif completely inhibited neurite outgrowth when added in solution at 0.5 μg/mL glucuronic acid concentration to hippocampal neurons (FIG. 5).

Glycopolymer 14 mimicked the activity of the natural polysaccharide (FIG. 5). While the isolated disaccharide 7 was insufficient for biological activity, incorporation of the disaccharide into a polymeric framework endowed it with the ability to inhibit neuronal growth. Moreover, the potency of the glycopolymers was valence-dependent: polymers with 25 disaccharide units exhibited moderate activity (40.9 (5.4% inhibition), while those with 80 disaccharide units showed significantly enhanced activity (86.0 (5.8% inhibition) at the same glucuronic acid concentration. These findings highlight the importance of multivalency in modulating the activity of CS. In addition, the unsulfated glycopolymer 15 had little effect on neurite outgrowth (5.9 (5.6% inhibition), confirming earlier observations that sulfation may be a prerequisite for activity, 4 and further highlighting the ability of these glycopolymers to recapitulate features of natural CS polysaccharides.

Previous studies have shown that a tetrasaccharide represents a minimum functional domain for protein recognition and neuronal growth-promoting activity when adhered to a substratum. In this solution-based assay, a monovalent tetrasaccharide at 0.5 μg/mL glucuronic acid concentration had minimal activity. In contrast, glycopolymer 16 at the same glucuronic acid concentration exhibited maximal activity, inducing neurite inhibition to the same extent as the natural polysaccharide (FIG. 5).

To compare the relative potencies of glycopolymer 16 and the natural polysaccharide, we measured their inhibition values at various concentrations (FIG. 6). We found that the inhibitory potency of 16 was comparable to that of the natural polysaccharide (IC50 values of 1.3 (0.1 and 1.2 (0.1 nM, respectively), despite considerable changes to the macromolecular structure. These results suggest flexibility in the way proteins engage CS. We find that a linear orientation of CS epitopes is not required for biological activity. Instead, strategic placement of short epitopes, even in the context of branched structures, is sufficient to recapitulate many of the properties of natural CS glycosaminoglycans.

Example 2

In Vivo Assay for Compound Effects in an Animal Model

The in vivo effect of compounds can be tested in an animal model. The choice of animal model will depend on the particular clinical indication or physiological readout being investigated. When assaying for an inhibitory effect on tumor growth, tumor animal models can be used, a vast number of which are known in the art. When assaying for the ability of the compounds to modulate neuronal growth, animal models for such utility can be selected, including but not limited to those animal models in which the neuronal cells are stained or marked with fluorescent proteins such as GFP.

The animal study typically begins with administering a subject compound into the subject animal. A variety of routes of administration are available in the art and described herein. After a suitable period post administration, the effect of such compounds can be assayed by immunostaining of affected tissues or cells, quantitative or qualitative assays for specific molecular markers by hybridization of transcripts or immunostaining of the resulting proteins.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sulfated glycosaminoglycan mimetic polymer having a plurality of repeating subunits, wherein an individual repeating subunit of said repeating subunits is a saccharide covalently linked to a backbone, wherein the number of repeating subunits in said polymer is m, and wherein the sulfated glycosaminoglycan mimetic polymer is of a formula:

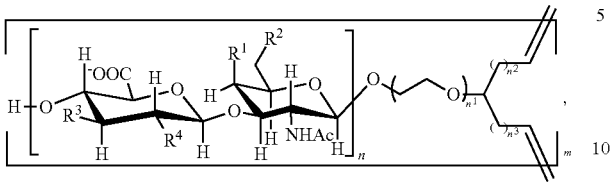

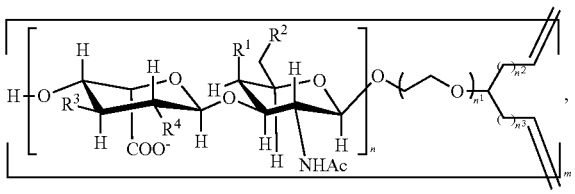

or

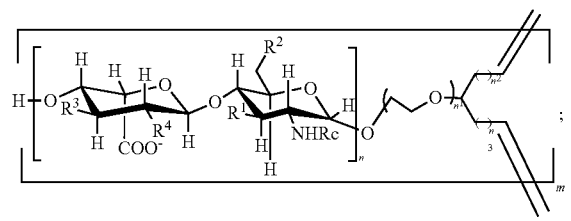

or a pharmaceutically acceptable salt or ester thereof;
wherein $R^1$, $R^2$, $R^3$, and $R^4$ are each independently selected from the group consisting of hydroxyl, sulfate, and phosphate;
one or more of $R^1$, $R^2$, $R^3$, and $R^4$ is a sulfate;
$R^6$ is selected from the group consisting of hydrogen, sulfite and acetyl;
n is 1 or greater;
wherein $n^1$ is between 1 and 25, $n^2$ is between 1 and 10, $n^3$ is between 1 and 10;
and m is 2 or greater.

2. The polymer of claim 1, wherein:
(a) $R^1$ and $R^2$ are each independently selected from sulfate and phosphate; and $R^3$ and $R^4$ are hydroxyl;
(b) $R^3$ and $R^4$ are each independently selected from sulfate and phosphate; and $R^1$ and $R^2$ are hydroxyl;

(c) $R^1$, $R^2$, and $R^3$ are each independently selected from sulfate and phosphate; and $R^4$ is hydroxyl;
(d) $R^1$, $R^2$, and $R^4$ are each independently selected from sulfate and phosphate; and $R^3$ is hydroxyl;
(e) $R^2$, and $R^4$ are each independently selected from sulfate and phosphate; and $R^1$, and $R^3$ are hydroxyl;
(f) $R^1$ is sulfate; and $R^2$, $R^3$, and $R^4$ are hydroxyl;
(g) $R^2$ is sulfate; and $R^1$, $R^3$, and $R^4$ are hydroxyl;
(h) $R^3$ is sulfate; and $R^1$, $R^2$, and $R^4$ are hydroxyl;
(i) $R^4$ is sulfate; and $R^1$, $R^2$, and $R^3$ are hydroxyl;
(j) $R^1$ and $R^3$ are each independently selected from sulfate, and phosphate; and $R^2$, and $R^4$ are hydroxyl;
(k) $R^1$ and $R^4$ are each independently selected from sulfate, and phosphate; and $R^2$, and $R^3$ are hydroxyl; or
(l) $R^2$ and $R^4$ are each independently selected from sulfate and phosphate; and $R^1$, and $R^3$ are hydroxyl;
and wherein
$R^6$ is selected from the group consisting of sulfite and acetyl.

3. The polymer of claim 1, wherein n is 10 or greater.
4. The polymer of claim 1, wherein n is 25 or greater.
5. The polymer of claim 1, wherein n is between 1 and 25.
6. The polymer of claim 1, wherein n is 1.
7. The polymer of claim 1, wherein n is 2.
8. The polymer of claim 1, wherein m is 5 or greater.
9. The polymer of claim 1, wherein m is 25 or greater.
10. The polymer of claim 1, wherein m is 50 or greater.
11. The polymer of claim 1, wherein m is 100 or greater.
12. The polymer of claim 1, wherein m is between 2 and 100.
13. A pharmaceutical composition comprising a polymer of claim 1 and a pharmaceutically acceptable carrier or excipient.
14. A composition comprising a population of the polymer of claim 1.
15. The composition of claim 14, wherein the composition has a polydispersity index less than 5.
16. The composition of claim 14, wherein the composition has a polydispersity index less than 2.
17. The composition of claim 14, wherein the composition has a polydispersity index less than 1.5.
18. The composition of claim 14, wherein the individual repeating subunits of said glycosaminoglycan mimetics bind to growth factors, neurotrophins, axon guidance proteins, inflammatory proteins, myelin associated proteins or their corresponding cell surface receptors.
19. The composition of claim 14, wherein the composition inhibits neural growth with an EC50 of 1 uM or less when assayed in an in vitro assay.
20. The composition of claim 19, wherein the EC50 is 25 nM or less.
21. The composition of claim 19, wherein the EC50 is 5 nM or less.
22. The composition of claim 14, wherein the composition stimulates neural growth with an EC50 of 1 uM or less when assayed in an in vitro assay.
23. The composition of claim 22, wherein the EC50 is 25 nM or less.
24. The composition of claim 22, wherein the EC50 is 5 nM or less.
25. A kit comprising a container containing a composition of claim 14; and instructions for use of said composition for inhibiting or stimulating neural growth.
26. A composition comprising a homogeneous population of the polymer of claim 1.
27. A method for obtaining a therapeutic benefit for an injury or disorder in a subject in need thereof, comprising

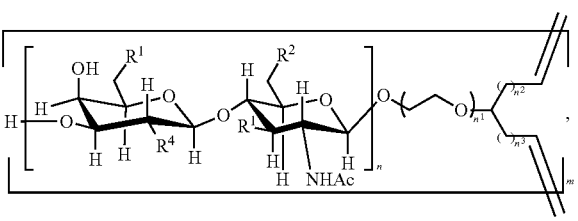

administering to said subject a therapeutically effective amount of the polymer of claim 1, wherein the injury or disorder is selected from the group consisting of Alzheimer's Disease, Parkinson's Disease, Huntington's Disease, amyotrophic lateral sclerosis, multiple sclerosis, spinal cord injury, neuronal injury, stroke, peripheral neuropathy, osteoarthritis, pulmonary embolism, and deep vein thrombosis.

28. A method for screening for glycomimetic stimulators or inhibitors of neural growth, wherein the method comprises: contacting cultured neurons with the polymer of claim 1, and determining an effect on neural growth in axon length relative to a control.

29. A method of modulating neural growth in a neural cell, wherein the method comprises administering an effective amount of the polymer of claim 1, wherein said neural cell is a brain cell, a stem cell, a central nervous system (CNS) cell, or a peripheral neural cell.

30. The method of claim 29, wherein the polymer promotes regeneration of an injured or severed nerve or nerve tissue or promotes outgrowth in said neural cell.

31. The method of claim 29, wherein the polymer promotes neural cell growth in a cultured neuron.

32. The method of claim 31, wherein the cultured neuron is a hippocampal neuron, dopaminergic neuron, dorsal root ganglion neuron, motor neuron, or sensory neuron.

* * * * *